(12) United States Patent
Yu et al.

(10) Patent No.: US 6,528,297 B1
(45) Date of Patent: Mar. 4, 2003

(54) HUMAN LYSOZYME GENE, ITS ENCODED POLYPEPTIDE AND THE METHOD FOR PREPARING THEM

(75) Inventors: Long Yu, Shanghai (CN); Qiang Fu, Shanghai (CN); Yong Zhao, Shanghai (CN); Honglai Zhang, Shanghai (CN); Anding Bi, Shanghai (CN)

(73) Assignee: Institute of Genetics Fudan University, Shanghai (CN)

( * ) Notice: Subject to any disclaimer, the term of this patent is extended or adjusted under 35 U.S.C. 154(b) by 0 days.

(21) Appl. No.: 09/786,003

(22) PCT Filed: Aug. 30, 1999

(86) PCT No.: PCT/CN99/00130
§ 371 (c)(1),
(2), (4) Date: Apr. 24, 2001

(87) PCT Pub. No.: WO00/12721
PCT Pub. Date: Mar. 9, 2001

(30) Foreign Application Priority Data

Aug. 31, 1998 (CN) .............................. 98111042

(51) Int. Cl.⁷ .............................. C12N 9/26; C12N 1/20; C12N 15/09; C12N 15/00; C07H 21/04

(52) U.S. Cl. .................. 435/201; 435/252.3; 435/320.1; 435/252.8; 536/23.2; 536/24.3; 536/24.1

(58) Field of Search .............................. 435/201, 252.3, 435/320.1, 252.8, 6; 536/23.2, 24.3, 24.1

(56) References Cited

U.S. PATENT DOCUMENTS 5,830,670 A * 11/1998 de la Monte et al. ...... 435/69.1

OTHER PUBLICATIONS

Online clipping from Entrez–PubMed, Dautigny et al., "cDNA and amino acid sequences of rainbow trout (*Oncorhynchus mykiss*) lysozymes and their implications for the evolution of lysozyme and lactalbumin", *J. Mol Evol.*, vol. 32, issue 2, pp. 187–198, Feb. 1991.

Online clipping from Entrez–PubMed, Weisman et al., "Evolutionary shift in the site of cleavage of prelysome", *J. Biol Chem*, vol. 261, issue 5, pp. 2309–2313, 1986.

Sava et al., "Lysozyme and Cancer: Role of Exogenous Lysozyme as Anticancer Agent (Review)", *Anticancer Research*, vol. 9, pp. 583–592, 1989.

"The Chemistry of Lysozyme and its use as a food preservative and a pharmaceutical", *Critical Review Food Science Nutrition*, vol. 26, issue 4, pp.359–395, 1988.

Printout from NCBI Sequence Viewer regarding AC004675, Bireen et al., "*Homo sapiens* chromosome 17, clone hCIT.186_H_2, complete sequence", Aug. 1998.

Printout from NCBI Sequence Viewer regarding P49663, Araki et al., Lysozyme C (1, ", 4–Beta–N–Acetylmuramidase) Feb. 1996.

Printout from NCBI Sequence Viewer regarding P00703, Weisman et al., "Lysozyme C. Presursor (1, 4–Beta–N–Acetylmuramidase C)", Jul. 1998.

Printout from NCBI Sequence Viewer regarding X59491, Dautigny et al., "*O.mykiss* mRNA for lysozyme II", Apr. 1992.

(List continued on next page.)

Primary Examiner—Ponnathapu Achutamurtry
Assistant Examiner—Yong Pak
(74) Attorney, Agent, or Firm—Baker Botts LLP

(57) ABSTRACT

The invention relates to a novel member LYC1 of lysozyme gene family. The invention provides the cDNA sequence encoding for the novel lysozyme, the polypeptide encoded by the sequence, as well as the method for producing the novel human lysozyrne utilizing recombinant technology. The invention also provides the use of the novel human lysozyme.

12 Claims, 1 Drawing Sheet

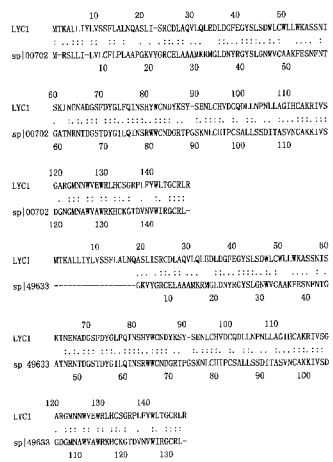

OTHER PUBLICATIONS

Printout from PIR Entry LZFER, by Weisman et al., "Lysozyme (EC 3. 2. 1. 17) c precursor ring–necked pheasant", Sep. 2000.

Hillier et al. EST database—Accession #AA400242 (1997).*

Castanon et al. Cloning of human lysozyme gene and expression in the yeast *Saccharomyces cerevisiae*. Gene, vol. 66, pp. 223–34, 1988.*

Miki et al. Construction of a plasmid vector of the regulatable high level expression of eukaryotic genes in *Escherichia coli*: an application to overproduction of chicken lysozyme. Protein Eng., vol. 14, pp. 327–32, 1987.*

Takayama et al. Antisense RNA. Crit Rev Biochem Mol Biol. 1990: p. 155–84.*

* cited by examiner

```
              10        20        30        40        50
LYC1     MTKALLIYLVSSFLALNQASLI-SRCDLAQVLQLEDLDGFEGYSLSDWLCWLLWKASSNI
            : ..::: ::  :: :    . . .::.:: ...    ::..,.:::::..:.:    .... :
sp|00702 M-RSLLI-LVLCFLPLAAPGKVYGRCELAAAMKRMGLDNYRGYSLGNWVCAAKFESNFNT
              10        20        30        40        50

60        70        80        90       100       110
LYC1     SKINENADGSFDYGLFQINSHYWCNDYKSY-SENLCHVDCQDLLNPNLLAGIHCAKRIVS
            .  :.:.::: :::..:::::..::::  ..   :.::::.  :.  ::.  .. :...:::.:::
sp|00702 GATNRNTDGSTDYGILQINSRWWCNDGRTPGSKNLCHIPCSALLSSDITASVNCAKKIVS
              60        70        80        90       100       110

120       130       140
LYC1     GARGMNNWVEWRLHCSGRPLFYWLTGCRLR
            . :::  ::  :: ::.:   .    :.  ::::
sp|00702 DGNGMNAWVAWRKHCKGTDVNVWIRGCRL-
            120       130       140
```

Fig. 1A

```
              10        20        30        40        50        60
LYC1     MTKALLIYLVSSFLALNQASLISRCDLAQVLQLEDLDGFEGYSLSDWLCWLLWKASSNIS
                                ... .:::.: ...     ::..,.:::::..:.:    .... : .
sp|49633 ------------------GKVYGRCELAAAMKRMGLDNYRGYSLGNWVCAAKFESNFNTG
                            10        20        30        40

70        80        90       100       110
LYC1     KINENADGSFDYGLFQINSHYWCNDYKSY-SENLCHVDCQDLLNPNLLAGIHCAKRIVSG
            :.  :.:.::: :::..:::::..::::  ..   :.::::.  :.  ::.  .. :...:::.:::
sp|49633 ATNRNTDGSTDYGILQINSRWWCNDGRTPGSKNLCHIPCSALLSSDITASVNCAKKIVSD
              50        60        70        80        90       100

120       130       140
LYC1     ARGMNNWVEWRLHCSGRPLFYWLTGCRLR
            . :::  ::  :: ::.:   .    :.  ::::
sp|49633 GDGMNAWVAWRKHCKGTDVNVWIRGCRL-
            110       120       130
```

Fig. 1B

HUMAN LYSOZYME GENE, ITS ENCODED POLYPEPTIDE AND THE METHOD FOR PREPARING THEM

This application is a National Stage application under 35 U.S.C. §371 of International Application Serial No. PCT/CN99/00130 filed Aug. 30, 1999 and published in Chinese as WO 00/12721 on Mar. 9, 2000, which claims priority to Chinese Application Serial No. 98111042.8, filed Aug. 31, 1998.

The invention relates to a new polynucletide, the polypeptide encoded by said polynucleotide, the uses of said polynucleotide and polypeptide, and the methods for preparing same. In particular, the invention relates to a new member of the lysozyme family.

Lysozyme exists ubiquitously in all parts of organisms, including various tissues, organs, and sera; it is especially abundant in egg white. Lysozyme is mainly secreted by the epithelial cell of certain glands and some kinds of leukocyte.

Lysozyme was first reported by Fleming, et al. in 1922. Afterward, lysozyme has been widely studied. A lot of papers concerning its crystal structure, protein catalytic domains, catalytic dynamics, immunology, molecular evolutionary, and so on, have been published. Lysozyme is one of the proteins that are studied most extensively and intensively. However, the study on lysozyme gene is not yet sufficient. Nowadays, only a few lysozyme genes from different species, such as *E.coli* T4, salmonella P22 phage, bacillus φ phage and chicken, etc., have been cloned. (1983 J. Mol. Biol. 165. 229–248; 1985 Virology 143, 280–289; 1987 Proc. Natl. Acad. Sci. USA, 77, 5759–5763). The cloning about human lysozyme gene was also reported (1988, Gene 66,223–234).

The main function of lysozyme is to hydrolyze the beta(1–4) glycosidic bond between N-acetylmuramic acid (NAM) and N-acetylgluconic acid (NAG) of the bacterial cell wall. In the organism, lysozyme can act as a nonspecific immune molecule against bacterial infections, and as a digestive enzyme in enteron and some mollusks which live on bacteria. Further, lysozyme has the function of inhibiting tumor growth. Therefore, lysozyme has important applications in both industry and medicine.

One purpose of the invention is to provide a new polynucleotide which encodes a new member of lysozyme gene family. The new human lysozyme is named LYC1.

Another purpose of the invention is to provide a new member of lysozyme protein family, which is named LYC1.

Still another purpose of the invention is to provide a new method for preparing said new human lysozyme by recombinant techniques.

The invention also relates to the uses of said human lysozyme and its coding sequence.

In one aspect, the invention provides an isolated DNA molecule, which comprises a nucleotide sequence encoding a polypeptide having human LYC1 protein activity, wherein said nucleotide sequence shares at least 70% homology to the nucleotide sequence of nucleotides 84–530 in SEQ ID NO: 4, or said nucleotide sequence can hybridize to the nucleotide sequence of nucleotides 84–530 in SEQ ID NO: 4 under moderate stringency. Preferably, said nucleotide sequence encodes a polypeptide comprising the amino acid sequence of SEQ ID NO: 5. More preferably, the sequence comprises the nucleotide sequence of nucleotides 84–530 in SEQ ID NO: 4.

Further, the invention provides an isolated LYC1 polypeptide, which comprises a polypeptide having the amino acid sequence of SEQ ID NO: 5, its active fragments, and its active derivatives. Preferably, the polypeptide is a polypeptide having the amino acid sequence of SEQ ID NO: 5.

The invention also provides a vector comprising said isolated DNA.

The invention further provides a host cell transformed with said vector.

In another aspect, the invention provides a method for producing a polypeptide with the activity of LYC1 protein, which comprises:

(a) forming an expression vector of LYC1 protein comprising the nucleotide sequence encoding the polypeptide having the activity of LYC1 protein, wherein said nucleotide sequence is operably linked with an expression regulatory sequences, and said nucleotide sequence shares at least 70% homology to the nucleotide sequence of positions 84–530 in SEQ ID NO: 4;

(b) introducing the vector of step (a) into a host cell, thereby forming a recombinant cell of LYC1 protein;

(c) culturing the recombinant cell of step (b) under the conditions suitable for the expression of LYC1 polypeptides;

(d) isolating the polypeptides having the activity of LYC1 protein.

In one embodiment of the present invention, the isolated polynucleotide has a full length of 583 nucleotides, whose detailed sequence is shown in SEQ ID NO: 4. The open reading frame (ORF) locates at nucleotides 84–530.

In the present invention, the term "isolated" or "purified" or "substantially pure" DNA refers to a DNA or fragment which has been isolated from the sequences which frank it in a naturally occurring state. The term also applied to DNA or DNA fragment which has been isolated from other components naturally accompanying the nucleic acid and from proteins naturally accompanying it in the cell.

In the present invention, the term "LYC1 protein encoding sequence" or "LYC1 polypeptide encoding sequence" refers to a nucleotide sequence encoding a polypeptide having the activity of LYC1 protein, such as the nucleotide sequence of positions 84–530 in SEQ ID NO: 4 or its degenerate sequence. The degenerate sequences refer to the sequences formed by replacingone or more codons in the ORF of 84–530 in SEQ ID NO: 4 with degenerate codes which encode the same amino acid. Because of the degeneracy of codon, the sequence having a homology as low as about 70% to the sequence of nucleotides 84–530 in SEQ ID NO: 4 can also encode the sequence shown in SEQ ID NO: 5. The term also refers to the nucleotide sequences that hybridize with the nucleotide sequence of nucleotides 84–530 in SEQ ID NO: 4 under moderate stringency or preferably under high stringency. In addition, the term also refers to the sequences having a homology at least 70%, preferably 80%, more preferably 90% to the nucleotide sequence of nucleotides 84–530 in SEQ ID NO: 4.

The term also refers to variants of the sequence in SEQ ID NO: 4, which are capable of coding for a protein having the same function as human LYC1 protein. These variants includes, but are not limited to: deletions, insertions and/or substitutions of several nucleotides (typically 1–90, preferably 1–60, more preferably 1–20, and most preferably 1–10) and additions of several nucleotides (typically less than 60, preferably 30, more preferably 10, most preferably 5) at 5' end and/or 3' end.

In the present invention, "substantially pure" proteins or polypeptides refers to those which occupy at least 20%, preferably at least 50%, more preferably at least 80%, most preferably at least 90% of the total sample material (by wet weight or dry weight). Purity can be measured by any appropriate method, e.g., in the case of polypeptides by column chromatography, PAGE or HPLC analysis. A substantially purified polypeptides is essentially free of naturally associated components.

In the present invention, the term "LYC1 polypeptide" or "LYC1 protein" refers to a polypeptide having the activity of LYC1 protein comprising the amino acid sequence of SEQ ID NO: 5. The term also comprises the variants of said amino acid sequence which have the same function of human lysozyme. These variants include, but are not limited to, deletions, insertions and/or substitutions of several amino acids (typically 1–50, preferably 1–30, more preferably 1–20, most preferably 1–10), and addition of one or more amino acids (typically less than 20, preferably less than 10, more preferably less than 5) at C-terminal and/or N-terminal. For example, the protein function are usually unchanged when an amino residue is substituted by a similar or analogous one. Further, the addition of one or several amino acids at C-terminal and/or N-terminal will not change the function of protein. The term also includes the active fragments and derivatives of LYC1 protein.

The variants of polypeptide include homologous sequences, allelic variants, natural mutants, induced mutants, proteins encoded by DNA which hybridizes to LYC1 DNA under high or low stringency conditions as well as the polypeptides or proteins retrieved by antisera raised against LYC1 polypeptide. The present invention also provides other polypeptides, e.g., fusion proteins, which include the LYC1 polypeptide or fragments thereof. In addition to substantially full-length polypeptide, the soluble fragments of LYC1 polypeptide are also provided. Generally, these fragments comprise at least 10, typically at least 30, preferably at least 50, more preferably at least 80, most preferably at least 100 consecutive amino acids of human LYC1 polypeptide.

The present invention also provides the analogues of LYC1 protein or polypeptide. Analogues can differ from naturally occurring LYC1 polypeptide by amino acid sequence differences or by modifications which do not affect the sequence, or by both. These polypeptides include genetic variants, both natural and induced. Induced variants can be made by various techniques, e.g., by random mutagenesis using irradiation or exposure to mutagens, or by site-directed mutagenesis or other known molecular biologic techniques. Also included are analogues which include residues other than those naturally occurring L-amino acids ( e.g., D-amino acids) or non-naturally occurring or synthetic amino acids (e.g., beta- or gamma-amino acids). It is understood that the polypeptides of the invention are not limited to the representative polypeptides listed hereinabove.

Modifications ( which do not normally alter primary sequence) include in vivo, or in vitro chemical derivation of polypeptides, e.g., acelylation, or carboxylation. Also included are modifications of glycosylation, e.g., those made by modifying the glycosylation patterns of a polypeptide during its synthesis and processing or in the further processing steps, e.g., by exposing the polypeptide to enzymes which affect glycosylation (e.g., mammalian glycosylating or deglycosylating enzymes). Also included are sequences which have phosphorylated amino acid residues, e.g., phosphotyrosine, phosphoserine, phosphothronine, as well as sequences which have been modified to improve their resistance to proteolytic degradation or to optimize solubility properties.

The invention also includes antisense sequence of the sequence encoding LYC1 polypeptide. Said antisense sequence can be used to inhibit expression of LYC1 in cells.

The invention also include probes, typically having 8–100, preferably 15–50 consecutive nucleotides. These probes can be used to detect the presence of nucleic acid molecules coding for LYC1 in samples.

The present invention also includes methods for detecting LYC1 nucleotide sequences, which comprises hybridizing said probes to samples, and detecting the binding of the probes. Preferably, the samples are products of PCR amplification. The primers in PCR amplification correspond to coding sequence of LYC1 polypeptide and are located at both ends or in the middle of the coding sequence. In general, the length of the primers is 20 to 50 nucleotides.

A variety of vectors known in the art, such as those commercially available, are useful in the invention.

In the invention, the term "host cells" includes prokaryotic and eukaryotic cells. The common prokaryotic host cells include *Escherichi coli, Bacillus subtilis*, and so on. The common eukaryotic host cells include yeast cells, insect cells, and mammalian cells. Preferably, the host cells are eukaryotic cells, e.g., CHO cells, COS cells, and the like.

In another aspect, the invention also includes antibodies, preferably monoclonal antibodies, which are specific for polypeptides encoded by LYC1 DNA or fragments thereof. By "specificity" is meant an antibody which binds to the LYC1 gene products or a fragments thereof. Preferably, the antibody binds to the LYC1 gene products or a fragments thereof and does not substantially recognize and bind to other antigenically unrelated molecules. Antibodies which bind to LYC1 and block LYC1 protein and those which do not affect the LYC1 function are included in the invention. The invention also includes antibodies which bind to the LYC1 gene product in its unmodified as well as modified form.

The present invention includes not only intact monoclonal or polyclonal antibodies, but also immunologically-active antibody fragments, e.g., a Fab' or (Fab)$_2$ fragment, an antibody light chain, an antibody heavy chain, a genetically engineered single chain Fv molecule (Lander, et al., U.S. Pat. No. 4,946,778), or a chimeric antibody, e.g., an antibody which contains the binding specificity of a murine antibody, but the remaining portion of which is of human origin.

The antibodies in the present invention can be prepared by various techniques known to those skilled in the art. For example, purified LYC1 gene products, or itsantigenic fragments can be administrated to animals to induce the production of polyclonal antibodies. Similarly, cells expressing LYC1 or its antigenic fragments can be used to immunize animals to produce antibodies. Antibodies of the invention can be monoclonal antibodies which can be prepared by using hybnrdoma technique (See Kohler, et al., Nature, 256; 495,1975; Kohler, et al., Eur. J. Immunol. 6: 511,1976; Kohler, et al., Eur. J. Immunol. 6: 292, 1976; Hammerling, et al., In Monoclonal Antibodies and T Cell Hybridomas, Elsevier, N.Y., 1981). Antibodies of the invention comprise those which block LYC1 function and those which do not affect LYC1 function. Antibodies in the invention can be produced by routine immunology techniques and using fragments or functional regions of LYC1 gene product. These fragments and functional regions can be prepared by recombinant methods or synthesized by a polypeptide synthesizer. Antibodies binding to unmodified LYC1 gene product can be produced by immunizing animals with gene products produced by prokaryotic cells (e.g., *E. coli*); antibodies binding to post-translationally modified forms thereof can be acquired by immunizing animals with gene products produced by eukaryotic cells (e.g., yeast or insect cells).

In one embodiment, the polynucleotide of the invention is 583 bp in full length whose detailed sequence is shown in SEQ ID NO: 4 with the ORF located at positions 84–530. Said polynucleotide was obtained as follows: human brain λ gt 11 cDNA library (Clontech) was used as a template and PCR was carried out with forward primer A1: 5'-TAAGGAAACCTGGCTGCCCTCTC-3'(SEQ ID NO: 1) and reverse primer B: 5'-CTGAGTGAGGACAGGAGTCTTGG-3'(SEQ ID NO: 2). Then, the PCR amplification product was used as a template and an additional PCR was carried out with primer A2: 5'CCAGGCTCTCAGAGAAGATCAGC-3'(SEQ ID NO: 3) and reverse primer B. Target fragments of 614 bp (product A1B) and 583 bp (product A2B) were obtained in two PCRs, respectively. The sequencing of the PCR product A2B gave the full length cDNA sequence shown in SEQ ID NO: 4.

Homology comparison showed that the nucleotide sequence and the coded protein sequence of the invention shared remarkable homology to other lysozymes from different origins. Therefore, it indicates it is a new member of lysozyme family and has some important functions of the family.

Lysozyme can lyse cells by hydrolyze the beta(1-4) glycosidic bond between N-acetylmuramic acid (NAM) and N-acetylgluconic acid (NAG) of the bacterial cell wall. In the organisms, lysozyme can act as a nonspecific immune molecule against bacterial infections, and as a digestive enzyme in enteron and some mollusks which live on bacteria. Further, lysozyme has the function of inhibiting tumor growth. In 1955, Caselli and Shumacher (Boll Ocul 34:513–533, 1955) reported on the lysozyme-mediated 70% inhibition of neoplastic transformation in cornea of chicken infected by Rous sarcoma virus. Many other experiments indicated that lysozyme participates in the process of tumor diffusion and interacts with phospho- and glucolipid molecule of tumor cells. The inhibition effect on human tumor of lysozyme was reported and patented (1980 Jpn Kokai, Tokkyo Koho 33,409; 1980 Jpn Kokai Tokkyo Koho 33,408). As to the mechanism of lysozyme inhibition on tumor, there are two possibilities: (1) lysozyme directly activates the organism's immunity functions; (2) lysozyme indirectly enhances the organism's immune ability (1989 Anticancer Research 9, 583–592).

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLES

Example 1
The Cloning and Sequencing of LYC1 cDNA Sequence
1. Amplification with Primers The template was human brain λ gt 11 cDNA library (commercially available from Clontech). PCR with forward primer A1: 5'-TAAGGAAACCTGGCTGCCCTCTC-3' (SEQ ID NO: 1) and reverse primer B: 5'-CTGAGTGAGGACAGGAGTCTTGG-3'(SEQ ID NO: 2) was carried out. The PCR condition for A1/B was 4 mins at 93° C.; followed by 35 cycles with 1 min at 93° C., 1 min at 70° C., at 72° C.; and, finally 5 mins at 72° C. Then, using the above PCR product as a template, an additional PCR was carried out with forward primer A2: 5'-CCAGGCTCTCAGAGAAGATCAGC-3'(SEQ ID NO: 3) and reverse primer B. The PCR condition was 4 mins at 93° C.; followed by 35 cycles with 1 min at 93° C., 1 min at 70° C., and 1 min at 72° C.; and, finally, 5 mins at 72° C. The PCR fragments were detected by electrophoresis. The target fragment amplified by primers A1 and B was 614 bp, and the fragment amplified by primers A2 and B was 583 bp.

2. Sequencing PCR Products

PCR products amplified by primers A2 and B were linked with pGEM-T® vector (Promega) and transformed into E. coli JM103. The plasmids were extracted using QIAprep Plasmid Kit (QIAGEN). The oriented serial deletion of the inserted fragments was carried out with Double-Stranded Nested Deletion Kit (Pharmacia), and the deletants were quickly identified by PCR and arranged in order. The deletants successively cut-off were sequenced with SequiTherm EXCEL™ DNA Sequencing Kit (Epicentre Technologies). A full length cDNA sequence of 583 bp was obtained by overlapping the sequences with computer software. The detailed sequence is shown in SEQ ID NO: 4 with an open reading frame (ORF) located at nucleotides 84–530.

According to the resultant full-length cDNA sequence, the amino acid sequence of LYC1 was deduced, having 148 amino acid residues totally. See SEQ ID NO: 5 for its amino acid sequence in details.

Example 2
Homologous Comparison

The full length cDNA sequence of LYC1 and the coded protein were used for homologous screening Non-redundant GenBank+EMBL+DDBJ+PDB and GenBank CDS translations+PDB+SwissProt+Spupdate+PIR databases by BLAST algorithm. The result showed that they shared high homology to other members of the lysozyme family. The amino acid sequence of LYC1 shares 46.3% identity and 60% similarity with ring-necked pheasant's lysozyme C (sp/p00702), and 45.4% identity and 59.2% similarity with lysozyme C of green pheasant (sp/p49663), when analyzed by PCGENE software.

In particular, in amino acid sequence of LYC1, there exists a 19 amino acids signature sequence of lysozyme and alpha-lactoalbumin: $CX_3CX_2(L/M/F)X_3(D/E/N)(L/I)X_5C$ [ Note: In the sequence, X represents any amino acid, digits such as "2" denote the number of amino acid, "(L/M/H)" represents any of these three amino acids]. Lysozyme and alpha-lactoalbumin are two proteins related closely in evolution (Eur. J. Biochem. 182: 111–118). In the protein of the present invention, the sequence matching the signature is: CHVDCQDLLNPNLLAGIHC (residues 94–112 in SEQ ID NO: 4). It indicates that the LYC1 of the present invention belongs to lysozyme family, and has the relative functions of the lysozyme family.

Lysozyme can lyse cells by hydrolyze the beta(1-4) glycosidic bond between N-acetylmuramic acid (NAM) and N-acetylgluconic acid (NAG) of the bacterial cell wall. In the organisms, lysozyme can act as a nonspecific immune molecule against bacterial infections, and as a digestive enzyme in enteron and some mollusks which live on bacteria.

Lysozyme has important applications in both industry and medicine.

First, in industry (mainly in food industry), lysozyme can be used as a preservative or additive for food. In this respect, the Japanese have developed many use of lysozyme and owe many patents. For example, they use lysozyme as a preservative for fresh fruit, vegetable, soybean milk, marine foods and meat. Lysozyme can also be used as an additive for infant's foods to simulate human milk (1988, Crit Rev Food Sci Nutr 26(4):359–395).

In respect of pharmaceutical use, lysozyme can be used to cure viral and bacterial infections. For example, EDTA-tris-lysozyme solutions are effective on the pseudomonas cystitis induced by *E.coli* infection. Lysozyme concentration in human and animal serum is an indicator of infection. Zajaczkowska-Bialowas and Murai studied the relationship between lysozyme activity in saliva and diseases of oral cavity. The result showed that lysozyme had obvious alleviation effect on the symptom of chronic periodontitis. Besides, they found the synergistic effects of lysozyme and some antibiotics. When lysozyme was used alone, even in a large amount, the bacteriolysis effect on *S. aureus* was little. But with the presence of amoxicillin, the lysis effect was enhanced and in proportion to the amount of lysozyme (1988 Crit Rev Food Sci Nutr 26(4):359–395).

Further, lysozyme has the function of inhibiting tumor growth. In 1955, Caselli and Shumacher (1955, Boll Ocul 34:513–533) reported on the lysozyme-mediated 70% inhibition of neoplastic transformation in cornea of chicken infected by *Rous sarcoma* virus. Many other experiments indicated that lysozyme had some relationship to the inhibition of tumor diffusion (1988 Clin. Expl. Metastasis 6:245–253; 1998 Folia Onclo 10, Suppl A: 219–224; 1988 Eur. J. Cancer Clin. Onco. 124:1737–1743). It is also found that lysozyme interacts with phospho- and glucolipid molecule of tumor cells. The lysozyme's inhibition effect on human tumor was reported. Laterza successfully cured a case of small intestine reticulation sarcoma with diffusion after operation and radiotherapy ( "Atti del II Simposium Intemazionale sul Lisozima ", Milano. 7–8–9 1961. Vol I, sez V, pp 49–50). Battaglia et al. found that, though lysozyme could not reduce the volume of tumor, it had distinct effects of pain-killing and helping recovery in curing carcinomas of stomach, prostate, uterus and mammary gland ( "Atti del H Simposium Internaionale sul Lisozima di Fleming", Milano. 3–4–5 1964. Vol I, sez IV, pp 69–76). In Japan, the application of lysozyme in curing cancer was patented (1980 Jpn Kokai Tokkyo Koho 33, 409; 1980 Jpn Kokai Tokkyo Koho 33,408). Besides, A. Vacca et al. in 1985 reported an attempt of curing multiple myeloma by chemoimmunology with oral lysozyme as an immunomodulating agent. Their experiments indicated that 50% of the patients treated with a large amount of lysozyme had improved immune ability as compared with the controls (Chemiother IV n.2:147–155,1985). As to the mechanism of lysozyme inhibition on tumor, there are two possibilities: (1) lysozyme directly activates the organism's immunity functions; (2) lysozyme indirectly enhances the organism's immune ability (1989 Anticancer Research 9, 583–592).

Example 3

Expression of LYC1 in *E. coli*

The cDNA sequence encoding LYC1 was amplified with oligonucleotide PCR primers corresponding to 5'- and 3'-end of said DNA sequence, using human brain λ gt 11 cDNA library (Clontech) as a template. The resultant product was used as an insertion fragment.

The sequence of 5'-end oligonucleotide primer was:

5'-GCTGGATCCATGACAAAGGCGCTACTCAT-3' (SEQ ID NO: 6).

This primer contained a cleavage site of restriction endonuclease BamH I, followed by 19 nucleotides of LYC1 coding sequence starting from the start codon.

The sequence of 3'-end primer was:

5'-CATGTCGACTCATCTCAGGCGGCATCCTG-3' (SEQ ID NO: 7).

This primer contains a cleavage site of restriction endonuclease SalI, a translation terminator and partial LYC1 coding sequence.

These cleavage sites of restriction endonuclease in primers corresponded to the cleavage sites in bacterial expression vector pQE-9 (Qiagen Inc., Chatsworth, Calif.). Vector pQE-9 encodes an antibiotic resistance (Amp'), a bacterial replication origin (orn), an IPTG-adjustable promotor/operon (P/O), a ribosome-binding site (RBS), a six-hisitine tag (6-His) and cloning sites of restriction endonuclease.

Vector pQE-9 and insertion fragments were digested by BamHI and SalI, and then linked together, ensuring that the open reading frame started from the bacterial RBS. Then, the linkage mixture was used to transform *E.coli* M15/rep4 (Qiagen) containing multi-copy of plasmid pREP4 which expressed repressor of lacI and was resistant to kanamycin (Kan'). Transformants were screened out in LB medium containing Amp and Kan. The positive clones of transformant were cultured overnight in LB liquid medium supplemented with Amp (100 ug/ml) and Kan (25 ug/ml). The plasmids were extracted. The size and direction of the inserted fragments were verified by HindIII digestion. The sequencing confirmed that LYC1 cDNA fragment was correctly inserted into the vector.

The overnight culture was 1:100–1:250 diluted, inoculated into large volume medium, and cultured until the 600nm optical density ($OD_{600}$) reached 0.4–0.6. IPTG (isopropylthio-beta-D-galactoside) was added to final concentration of 1 mM. By deactivating repressor of LacI, IPTG induced and promoted P/O, thereby increasing the expression of gene. The cells were cultured for another 3-4 hours, and then centrifuged (6000×g, 20 mins). The inclusions were sonicated, and cell was collected and precipitates was solved in 6 M guanidine hydrochloride. After clarification, the dissolved LYC1 in solution were purified by nickel-chelated column chromatography under the conditions suitable for the tight binding of 6-His tagged protein and column. LYC1 was eluted with 6 M-guanidine hydrochloride (pH 5.0). The denaturalized proteins in guanidine hydrochloride were precipitated by several methods. First, guanidine hydrochloride was separated by dialysis. Alternatively, the purified protein, which was isolated from nickel-chelated column, bound to the second column with decreased linear gradient of guanidine hydrochloride. The proteins were denatured when binding to the column, and then eluted with guanidine hydrochloride (pH 5.0). Finally, the soluble proteins were dialyzed with PBS, then preserved in glycerol stock solution with the final glycerol concentration of 10% (w/v).

The molecular weight of the expressed protein was about 17 kDa, as identified by 12% SDS-PAGE.

Moreover, the sequencing results of the 10 amino acids at the N- and C-terminal of the expressed protein indicated that they were identical to those in SEQ ID NO: 5.

Example 4

Expression of LYC1 in Eukaryotic Cells (CHO Cell Line)

In this example, the cDNA sequence encoding LYC1 was amplified with oligonucleotide PCR primers corresponding to 5'- and 3'-end of said DNA sequence, using human brain λ gt 11 cDNA library (Clontech) as a template. The resultant product was used as an insertion fragment.

The sequence of 5'-end oligonucleotide primer was:

5'-GCTAAGCTTATGACAAAGGCGCTACTCAT-3' (SEQ ID NO: 8),

This primer contained a cleavage site of restriction endonuclease HindIII, followed by 20 nucleotides of LYC1 coding sequence starting from the start codon.

The sequence of 3'-end primer was:
5'-CATGGATCCTCATCTCAGGCGGCATCCTG-3' (SEQ ID NO: 9)

The primer contained a cleavage site of restriction endonuclease BamHI, a translation stop codon, and partial LYC1 coding sequence.

These cleavage sites of restriction endonuclease in primers corresponded to the cleavage sites in expression vector pcDNA3 for CHO cell. This vector encoded two kinds of antibiotic resistance (Amp$^r$ and Neo$^r$), a phage replication origin (fl ori), a virus replication origin (SV40 ori), a T7 promoter, a virus promoter (P-CMV), a Sp6 promoter, a polyadenylation signal of SV40 and the corresponding polyA sequence thereof, a polyadenylation signal of BGH and the poly A sequence thereof.

The vector pcDNA3 and insertion fragment were digested with HindIII and BainHI, and linked together. Subsequently, *E.coli* strand DH5 α was transformed with linkage mixture. Transformants were screened out in LB medium containing Amp. The clones containing the needed constructs were cultured overnight in LB liquid medium supplemented with Amp (100 ug/ml). Plasmids were extracted. The sequencing indicated that LYC1 cDNA fragment was correctly inserted into the vector.

Plasmids were transfected into CHO cells by lipofection with Lipofectin Kit (GIBco Life). After transfecting the cells for 48 hours and screening the cells with G418 for 2–3 weeks, the cells and cell supernatant were collected and the enzyme activity of the expressed protein was measured. G418 was removed and the transformnants were subcultured continuously. The mixed clonal cells were limiting diluted and the subclones with higher protein activity were selected. The positive subclones were mass cultured by routine methods. 48 hours later, the cells and supernatant were collected. The cells were ultrasonicated. Using 50mM Tris-HCl (pH7.6) solution containing 0.05% Triton as an equilibrium solution and eluent, the active peek of the protein was collected with a pre-balanced Superdex G-75 column. Then, using 50 mM Tris-HCl (pH8.0) solution containing 0-1 M NaCl as an eluent, the protein was gradiently washed on a DEAE-Sepharose column balanced with 50 mM Tris-HCl (pH8.0) solution. The active peek of the protein was collected. The solution of the expressed protein was dialyzed with PBS (pH7.4), and finally lyophilized and preserved.

The molecular weight of the expressed protein was about 17 kDa as identified by 12% SDS-PAGE.

Moreover, the sequencing results of the 10 amino acids at the N- and C-terminal of the expressed protein indicated that they were identical to those in SEQ ID NO: 5.

Example 5

Antibody Preparation

Antibodies were produced by immunizing animals with the recombinant proteins obtained in the above examples. The method was as follows: the recombinant proteins were isolated by chromatography, and stored for use. Alternatively, the protein was isolated by SDS-PAGE electrophoresis, and obtained by cutting eletrophoretic bands from gel. The protein was emulsified with Freund's complete adjuvant of the same volume. The emulsified protein was injected intraperitoneally into mice at a dosage of 50–100 ug/0.2 ml. 14 days later, the same antigen was emulsified with Freund's incomplete adjuvant and injected intraperitoneally into mice at a dosage of 50–100 ug/0.2 ml for booster immunization. Booster immunization was carried out every 14 days, for at least three times. The specific activity of the obtained antiserum was evaluated by its ability of precipitating the translation product of LYC1 gene in vitro.

All the documents cited herein are incorporated into the invention as reference, as if each of them is individually incorporated. Further, it is appreciated that, in the above teaching of the invention, the skilled in the art can make certain changes or modifications to the invention, and these equivalents are still within the scope of the invention defined by the appended claims of the present application.

What is claimed is:

1. An isolated nucleic acid molecule having a nucleotide sequence encoding a polypeptide having the lysozyme activity of a human LYC1 protein, said polypeptide having an amino acid sequence selected from the group consisting of SEQ ID NO: 5 and amino acids 20–148 in SEQ D NO: 5.

2. The isolated nucleic acid molecule of claim 1, wherein the polypeptide has the amino acid sequence of amino acids 20–148 in SEQ ID NO: 5.

3. An isolated LYC1 polypeptide comprising a polypeptide having an amino acid sequence selected from the group consisting of SEQ ID NO: 5, amino acids 20–148 of SEQ ID NO: 5, and active fragments thereof.

4. The isolated LYC1 polypeptide of claim 3, wherein the polypeptide has the amino acid sequence of SEQ ID NO: 5 or of amino acids 20–148 of SEQ ID NO: 5.

5. A vector containing the nucleic acid of claim 1.

6. A host cell transformed by the vector of claim 5.

7. The host cell of claim 6 wherein it comprises *E.coli*.

8. The host cell of claim 6 wherein it comprises a eukaryotic cell.

9. A method for producing a polypeptide having the lysozyme activity of a LYC1 protein comprising:

(a) forming an epression vector comprising an expression control sequence operably linked to a nucleotide sequence encoding a polypeptide having human LYC1 protein activity, said polypeptide having an amino acid sequence selected from the group consisting of SEQ ID NO: 5 and amino acids 20–148 of SEQ ID NO: 5;

(b) introducing the vector of step (a) into a host cell, thereby forming a recombinant cell capable of expressing LYC1 protein;

(c) culturing the recombinant cell of step (b) under conditions suitable for expression of LYC1 polypeptides;

(d) isolating polypeptide(s) having the lysozyme activity of a LYC1 protein.

10. The method of claim 9 wherein said nucleotide sequence comprises nucleotides 84–530 of SEQ ID NO: 4.

11. A nucleic acid molecule having the antisense sequence of the nucleic acid molecule of claim 1.

12. An isolated mucleic acid molecule having a nucleotide sequence encoding a polypeptide having the lysozyme activity of a human LYC1 protein, said nucleic acid having the nucleotide sequence of nucleotides 84–530 of SEQ ID NO: 4.

* * * * *

SEQUENCE LISTING

<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: SYNTHETIC PCR PRIMER

<400> SEQUENCE: 1
taaggaaacc tggctgccct ctc                                    23

<210> SEQ ID NO 2
<211> LENGTH: 23
<212> TYPE: DNA
<213> ORGANISM: Artificial Sequence
<220> FEATURE:
<223> OTHER INFORMATION: SYNTHETIC PCR PRIMER

<400> SEQUENCE: 2
ctgagtgagg acaggagtct tgg                                    23

<210> SEQ ID NO 3

```
<211> LENGTH: 23
<212> TYPE: DNA
<213> ORGANISM: Artificial Sequence
<220> FEATURE:
<223> OTHER INFORMATION: SYNTHETIC PCR PRIMER

<400> SEQUENCE: 3
ccaggctctc agagaagatc agc                                              23

<210> SEQ ID NO 4
<211> LENGTH: 583
<212> TYPE: DNA
<213> ORGANISM: HUMAN
<220> FEATURE:
<223> OTHER INFORMATION:

<400> SEQUENCE: 4
ccaggctctc agagaagatc agcagaaagt ctgcaagacc ctaagaacca tcagccctca      60
gctgcacctc ctcccctcca aggatgacaa aggcgctact catctatttg gtcagcagct    120
ttcttgccct aaatcaggcc agcctcatca gtcgctgtga cttggcccag gtgctgcagc    180
tggaggactt ggatgggttt gagggttact ccctgagtga ctggctgtgc tggcttttgt    240
ggaaagcaag ttcaaacata tcaaagataa atgaaaatgc ggatggaagc tttgactatg    300
gcctcttcca gatcaacagc cactactggt gcaacgatta taagagttac tcggaaaacc    360
tttgccacgt agactgtcaa gatctgctga atcccaacct tcttgcaggc atccactgcg    420
caaaaaggat tgtgtccgga gcacggggga tgaacaactg ggtagaatgg aggttgcact    480
gttcaggccg gccactcttc tactggctga caggatgccg cctgagatga aacagggtgc    540
gggtgcaccg tggagtcatt ccaagactcc tgtcctcact cag                      583

<210> SEQ ID NO 5
<211> LENGTH: 148
<212> TYPE: PRT
<213> ORGANISM: HUMAN
<220> FEATURE:
<223> OTHER INFORMATION:

<400> SEQUENCE: 5

Met Thr Lys Ala Leu Leu Ile Tyr Leu Val Ser Ser Phe Leu Ala Leu
 1               5                  10                  15

Asn Gln Ala Ser Leu Ile Ser Arg Cys Asp Leu Ala Gln Val Leu Gln
             20                  25                  30

Leu Glu Asp Leu Asp Gly Phe Glu Gly Tyr Ser Leu Ser Asp Trp Leu
         35                  40                  45

Cys Trp Leu Leu Trp Lys Ala Ser Ser Asn Ile Ser Lys Ile Asn Glu
     50                  55                  60

Asn Ala Asp Gly Ser Phe Asp Tyr Gly Leu Phe Gln Ile Asn Ser His
 65                  70                  75                  80

Tyr Trp Cys Asn Asp Tyr Lys Ser Tyr Ser Glu Asn Leu Cys His Val
                 85                  90                  95

Asp Cys Gln Asp Leu Leu Asn Pro Asn Leu Leu Ala Gly Ile His Cys
            100                 105                 110

Ala Lys Arg Ile Val Ser Gly Ala Arg Gly Met Asn Asn Trp Val Glu
        115                 120                 125

Trp Arg Leu His Cys Ser Gly Arg Pro Leu Phe Tyr Trp Leu Thr Gly
    130                 135                 140

Cys Arg Leu Arg
145
```

```
<210> SEQ ID NO 6
<211> LENGTH: 29
<212> TYPE: DNA
<213> ORGANISM: Artificial Sequence
<220> FEATURE:
<223> OTHER INFORMATION: SYNTHETIC PCR PRIMER

<400> SEQUENCE: 6
gctggatcca tgacaaaggc gctactcat                              29

<210> SEQ ID NO 7
<211> LENGTH: 29
<212> TYPE: DNA
<213> ORGANISM: Artificial Sequence
<220> FEATURE:
<223> OTHER INFORMATION: SYNTHETIC PCR PRIMER

<400> SEQUENCE: 7
catgtcgact catctcaggc ggcatcctg                              29

<210> SEQ ID NO 8
<211> LENGTH: 29
<212> TYPE: DNA
<213> ORGANISM: Artificial Sequence
<220> FEATURE:
<223> OTHER INFORMATION: SYNTHETIC PCR PRIMER

<400> SEQUENCE: 8
gctaagctta tgacaaaggc gctactcat                              29

<210> SEQ ID NO 9
<211> LENGTH: 29
<212> TYPE: DNA
<213> ORGANISM: Artificial Sequence
<220> FEATURE:
<223> OTHER INFORMATION: SYNTHETIC PCR PRIMER

<400> SEQUENCE: 9
catggatcct catctcaggc ggcatcctg                              29

<210> SEQ ID NO 10
<211> LENGTH: 26
<212> TYPE: DNA
<213> ORGANISM: Artificial Sequence
<220> FEATURE:
<223> OTHER INFORMATION: SYNTHETIC PCR PRIMER

<400> SEQUENCE: 10
gctaagctta gcctcatcag tcgctg                                 26
```